(12) United States Patent
Ek et al.

(10) Patent No.: US 10,350,078 B2
(45) Date of Patent: Jul. 16, 2019

(54) DEVICES, APPARATUSES, KITS, AND METHODS FOR REPAIR OF ARTICULAR SURFACE AND/OR ARTICULAR RIM

(71) Applicant: ARTHROSURFACE, INC., Franklin, MA (US)

(72) Inventors: Steven Ek, Bolton, MA (US); Anthony Miniaci, Bentleyville, OH (US); Tim Brightman, Franklin, MA (US)

(73) Assignee: ARTHROSURFACE, INC., Franklin, MA (US)

( * ) Notice: Subject to any disclaimer, the term of this patent is extended or adjusted under 35 U.S.C. 154(b) by 0 days.

(21) Appl. No.: 14/535,053

(22) Filed: Nov. 6, 2014

(65) Prior Publication Data

US 2015/0157462 A1 Jun. 11, 2015

Related U.S. Application Data

(63) Continuation-in-part of application No. 13/923,915, filed on Jun. 21, 2013, now Pat. No. 9,668,757.

(60) Provisional application No. 61/665,092, filed on Jun. 27, 2012.

(51) Int. Cl.
*A61F 2/30* (2006.01)
*A61F 2/40* (2006.01)
*A61B 17/17* (2006.01)
*A61B 17/88* (2006.01)
*A61B 90/00* (2016.01)
*A61B 50/30* (2016.01)

(52) U.S. Cl.
CPC ........ *A61F 2/4081* (2013.01); *A61B 17/1739* (2013.01); *A61F 2/30734* (2013.01); *A61B 17/1778* (2016.11); *A61B 17/8897* (2013.01); *A61B 50/30* (2016.02); *A61B 2090/033* (2016.02); *A61B 2090/062* (2016.02); *A61F 2002/3092* (2013.01); *A61F 2002/30281* (2013.01); *A61F 2002/30736* (2013.01); *A61F 2002/30784* (2013.01); *A61F 2002/30841* (2013.01)

(58) Field of Classification Search
CPC .. A61F 2002/30281; A61F 2002/30736; A61F 2002/30784; A61F 2002/3092; A61F 2/4081
See application file for complete search history.

(56) References Cited

U.S. PATENT DOCUMENTS

| 4,959,072 A | * | 9/1990 | Morscher | ........... | A61B 17/8066 |
| | | | | | 623/22.11 |
| 2005/0182493 A1 | * | 8/2005 | Bertram, III | ....... | A61B 17/1746 |
| | | | | | 623/22.38 |

(Continued)

OTHER PUBLICATIONS

Adbelhady, "Neglected anterior shoulder dislocation: open remplissage of the Hill-Sachs lesion with the infraspinatus tendon", *Acta Ortop Belg*, 76(2):162-16, 2010.

(Continued)

*Primary Examiner* — Samuel S Hanna
(74) *Attorney, Agent, or Firm* — Norton Rose Fulbright US LLP (57) ABSTRACT

Embodiments of devices, apparatuses, kits, and methods for repairing and/or augmenting the articular surface and/or articular rim of a joint (e.g., repairing the anterior glenoid rim after an anterior shoulder dislocation).

19 Claims, 11 Drawing Sheets

(56) References Cited

U.S. PATENT DOCUMENTS

| | | | | |
|---|---|---|---|---|
| 2007/0270853 | A1* | 11/2007 | Leung | A61B 17/80 606/69 |
| 2008/0243127 | A1* | 10/2008 | Lang | A61B 5/4528 606/87 |
| 2008/0269906 | A1* | 10/2008 | Iannotti | A61F 2/30942 623/19.11 |
| 2010/0069974 | A1* | 3/2010 | Oren | A61B 17/1714 606/86 R |
| 2010/0222782 | A1 | 9/2010 | Collazo | |
| 2010/0268238 | A1 | 10/2010 | Sikora | |
| 2011/0184419 | A1 | 7/2011 | Meridew | |
| 2012/0053590 | A1* | 3/2012 | Allen | A61B 17/1746 606/87 |
| 2012/0109331 | A1* | 5/2012 | Meridew | A61F 2/30756 623/22.21 |
| 2012/0158610 | A1* | 6/2012 | Botvinick | G06Q 10/0838 705/341 |
| 2012/0232656 | A1* | 9/2012 | Gedet | A61F 2/3872 623/14.12 |
| 2012/0283840 | A1* | 11/2012 | Frederick | A61F 2/32 623/22.32 |
| 2013/0158610 | A1* | 6/2013 | Hernandez | A61F 2/4081 606/315 |

OTHER PUBLICATIONS

Armitage et al., "An Anatomic, computed Tomographic Assessment of the Coracoid Process With Special Reference to the Congruent-Arc Latarjet Procedure", *Arthroscopy: The Journal of Arthroscopic and Related Surgery*, 27(11):1485-1489, 2011.

Boileau et al., "Arthroscopic Bankart-Bristow-Latarjet (2B3) Procedure: How to Do It and Tricks to Make it Easier and Safe", *Orthop clin N Am*, 41:381-392, 2010.

Boons et al., "Classic Versus Congruent Coracoid Positioning During the Latarjet Procedure: An In Vitro Biomechanical Comparison", *Arthroscopy: The Journal of Arthroscopic and Related Surgery*, 29(2):309-316, 2013.

Cadet, "Evaluation of Glenohumeral Instability", *Orthop Clin N Am*, 41:487-295, 2010.

De Beer and Roberts, "Glenoid Bone Defects—Open Latarjet with Congruent Arc Modification", *Orthop Clin N Am*, 41:407-415, 2010.

Degen et al., "A biomechanical assessment of superior shoulder translation after reconstruction of anterior glenoid bone defects: The Latarjet procedure versus allograft reconstruction", *Int. J. Shoulder Surg.*, 7(1):7-13, 2013.

Di Giacomo et al., "Coracoid bone graft osteolysis after Latarjet procedure: A comparison study between two screws standard technique vs mini-plate fixation", *Int. J. Shoulder Surg.*, 7(1):1-6, 2013.

Doursounian et al., "Bristow-Latarjet procedure with specific instrumentation: study of 34 cases", *International Orthopaedics (SICOT)*, 33:1031-1036, 2009.

Ettore et al., "Arthroscopically assisted Latarjet procedure: A new surgical approach for accurate coracoid graft placement and compression", *Int. J. Shoulder Surg.*, 7(3):120-123, 2013.

Itoi et al., "Bone loss in anterior instability", *Curr. Rev. Musculoskelet. Med.*, 6:88-94, 2013.

Ladermann et al., "Injury of the Suprascapular Nerve During Latarjet Procedure: An Anatomic Study", *Arthroscopy: The Journal of Arthroscopic and Related Surgery*, 28(3):316-321, 2012.

Lafosse et al., "Arthroscopic Latarjet Procedure", *Orthop Clin N Am*, 41:393-405, 2010.

Matthes et al., "Oldie but goldie: Bristow-Latarjet procedure for anterior shoulder instability", *Journal of Orthopaedic Surgery*, 15(1):4-8, 2007.

Maynou et al., "Function of subscapularis after surgical treatment for recurrent instability of the shoulder using a bone-block procedure", *The Journal of Bone & Joint Surgery (BR)*, 87-B:1096-1101, 2005.

Mercier and Saragaglia, "Mini-Open Latarjet Procedure for Recurrent Anterior Shoulder Instability", *SAGE—Hindawi Access to Research Advances in Orthopedics*, 6 pages, 2011.

Moros and Ahmad, "Partial Humeral Head Resurfacing and Latarjet Coracoid Transfer for Treatment for Recurrent Anterior Glenohumeral Instability", *Orthopedics*, 32(8), 4 pages, 2009.

Provencher et al., "Arthroscopic Management of Anterior Instability: Pearls, Pitfalls, and Lessons Learned", *Orthop Clin N Am*, 41:325-337, 2010.

Schulze-Borges et al., "Biomechanical Comparison of Open and Arthroscopic Latarjet Procedures", *Arthroscopy: The Journal of Arthroscopic and Related Surgery*, 29(4):630-637, 2013.

Weppe et al., "Biomechanical Evaluation of Bicortical Metal Screw Fixation Versus Absorbable Interference Screw Fixation After Coracoid Transfer for Anterior shoulder Instability", *Arthroscopy: The Journal of Arthroscopic and Related Surgery*, 27(10):1358-1363, 2011.

* cited by examiner

DEVICES, APPARATUSES, KITS, AND METHODS FOR REPAIR OF ARTICULAR SURFACE AND/OR ARTICULAR RIM

CROSS-REFERENCE TO RELATED APPLICATIONS

This application is a continuation-in-part of U.S. patent application Ser. No. 13/923,915 filed Jun. 21, 2013, which claims priority to U.S. Provisional Application No. 61/665,092, filed Jun. 27, 2012, both of which are incorporated by reference in their entireties.

BACKGROUND

1. Field of the Invention

The present invention relates generally to orthopedic treatments, and more particularly, but not by way of limitation, to devices, apparatuses, kits, and methods for repairing and/or augmenting the articular surface and/or articular rim of a joint.

2. Description of Related Art

One example of a method for repairing (e.g., after a fracture resulting from an anterior shoulder dislocation) the rim of a patient's glenoid (glenoid fossa) is known as the Laterjet procedure, in which a portion of a patient's coracoid process is removed and attached to the clavicle in a position where a portion of the glenoid rim has previously broken off, to augment the anterior glenoid and stabilize the humeral head in the shoulder joint. Fitting the removed portion of the coracoid process to the anterior glenoid rim involves a trial-and-error approach that requires a surgeon (or other healthcare provider) to iteratively shape the removed portion of the coracoid process to the anterior glenoid to augment the glenoid rim without interfering with motion of the joint. This trial-and-error approach may, in some instances, be complicated by variations in coracoid shape.

SUMMARY

This disclosure includes embodiments of devices, apparatuses, kits, and methods for repairing and/or augmenting the articular surface and/or articular rim of a joint.

Some embodiments of the present devices comprise: a pre-formed body comprising a coupling side and a concave side disposed at a non-parallel angle relative to the coupling side such that the angle between the coupling side and the concave side is greater than 60 degrees, the body configured to be coupled to a bone adjacent to a selected type of human joint socket such that the coupling side faces the bone and the concave side augments the articular surface of the joint. In some embodiments, the body is configured to be coupled to a scapula adjacent the glenoid such that the concave side augments an anterior portion of the glenoid rim. In some embodiments, the body comprises one or more holes extending through the body without extending through the concave side such that the body can be coupled to the bone by one or more screws extending through the one or more holes. In some embodiments, the one or more holes each has a central longitudinal axis that is perpendicular to the coupling side. In some embodiments, the body comprises a biological material. In some embodiments, the material comprises cortical bone. In some embodiments, the concave side is substantially smooth. In some embodiments, the body further includes an outer side that cooperates with the concave side to form an outer rim, and the coupling side and concave side cooperate to form an inner rim. In some embodiments, the inner rim is concave and the outer rim is convex. Some embodiments further comprise two or more suture holes each extending through the body without extending through the concave side. In some embodiments, the suture holes are adapted to suture soft tissue adjacent to the joint.

Some embodiments of the present apparatuses comprise: a jig having a body and a handle extending from the body, the body having a first side and a second side, the first side configured to be disposed in contact with an articular surface of a selected type of human joint socket, the handle defining one or more elongated channels each extending longitudinally through the handle and offset from the first side of the body such that if the first side of the body is disposed in contact with an articular surface of the selected type of human joint socket, a central longitudinal axis will extend into bone adjacent the joint socket without passing through the articular surface. In some embodiments, the first side is configured to be disposed in contact with a glenoid such that the central longitudinal axis of each of the one or more elongated channels extends through the scapula adjacent the glenoid. In some embodiments, the first side is disposed relative to the central longitudinal axis of the channels such that the angle between the first side and the central longitudinal axis is between 0 and 10 degrees. In some embodiments, at least a portion of the first side is convex.

Some embodiments of the present apparatuses further comprise: a pin having a first end, a second end, and a depth indicator, the pin configured to be inserted into the bone adjacent the selected type of human joint socket through one of the one or more elongated channels in the handle of the jig to a depth indicated by the depth indicator such that the second end of the pin extends a predetermined distance out of the bone. In some embodiments, the depth indicator comprises a mark on the pin corresponding to a portion of the proximal end of the handle of the jig. Some embodiments further comprise: a reamer configured to be disposed over the second end of one of the pins when the first end of the pin is disposed in the bone, and rotated to remove a portion of the bone to form a mating surface on the bone. In some embodiments, the reamer comprises a cutting end, a distal end, and an elongated passage extending from the cutting end toward the distal end, the passage configured to receive at least a portion of one of the one or more pins. In some embodiments, the reamer comprises a shoulder in the passage, the shoulder configured to contact the second end of the pin to limit the depth to which the cutting end can cut. In some embodiments, the shape of the mating surface corresponds to the shape of the coupling side of the body of one of the present devices. In some embodiments, the mating surface and the coupling side are each substantially planar. In some embodiments, the length of said elongated channel is at least 5 centimeters.

Some embodiments of the present kits comprise: an embodiment of the present devices; and an embodiment of the present apparatuses. In some embodiments, the device and apparatus are sterile. In some embodiments, the device and apparatus are disposed in a sealed package.

Some embodiments of the present methods (e.g., of repairing a human joint socket) comprise: coupling a device having a pre-formed body to a bone adjacent to a human joint socket, where the body comprises a coupling side and a concave side disposed at a non-parallel angle relative to the coupling side such that the angle between the coupling side and the concave side is greater than 60 degrees, and the body is coupled to the bone such that the coupling side faces the bone and the concave side augments the articular surface of the joint socket. Some embodiments further comprise: shaping, prior to coupling the body to the bone, the bone to correspond to the shape of the coupling side. In some embodiments, shaping comprises: disposing a jig of the present apparatuses such that the first side contacts the articular surface of the joint socket; inserting a pin of the present apparatuses into the bone through one of the one or more elongated channels of the handle of the jig to a depth indicated by the depth indicator; removing the jig while the pin is disposed in the bone; disposing a reamer of the present apparatuses over the second end of the pin and rotating the reamer to shape the bone; and removing the reamer and the pin. In some embodiments, the one or more elongated channels in the handle of the jig comprises two holes, and shaping further comprises: inserting a pin of the present apparatuses into the bone through a second one of the one or more elongated channels in the handle of the jig to a depth indicated by the depth indicator; removing the jig while the second pin is disposed in the bone; disposing a reamer of the present apparatuses over the second end of the second pin and rotating the reamer to shape the bone; and removing the reamer and the second pin. In some embodiments, coupling comprises inserting one or more screws through the body and into the bone. In some embodiments, the preformed body comprises the pre-formed body of the device. In some embodiments, the joint socket comprises the glenoid, and where the body is coupled to the bone in which a portion of the glenoid rim is missing.

Some embodiments of the present devices comprise: a pre-formed body comprising a coupling side and a concave side disposed at a non-parallel angle relative to the coupling side, the body configured to be coupled to a bone adjacent to a selected type of human joint socket such that the coupling side faces the bone and the concave side augments the articular surface of the joint. In some embodiments, the body is configured to be coupled to a scapula adjacent the glenoid such that the concave side augments an anterior portion of the glenoid rim. In some embodiments, the body comprises one or more holes extending through the body without extending through the concave side such that the body can be coupled to the bone by one or more screws extending through the one or more holes. In some embodiments, the one or more holes each has a central longitudinal axis that is not perpendicular to the coupling side. In some embodiments, the body comprises a plurality of projections extending outwardly from the coupling side and configured to resist movement of the body relative to the bone. In some embodiments, the body comprises a non-biological material. In some embodiments, the material comprises steel. In some embodiments, the coupling side is configured to permit bone ingrowth into the body. In some embodiments, at least a portion of the coupling side is at least one of porous and etched. In some embodiments, the body comprises a structural material and a coating material. In some embodiments, the coating material covers substantially all of the concave side but does not cover substantially all of the coupling side. In some embodiments, the structural material comprises one or more pores or passages. In some embodiments, the concave side is substantially smooth. In some embodiments, the body further includes an outer side that cooperates with the concave side to form an outer rim, and the coupling side and concave side cooperate to form an inner rim. In some embodiments, the inner rim is concave and the outer rim is convex.

Some embodiments of the present apparatuses comprise: a jig having a body with a first side and a second side, the first side configured to be disposed in contact with an articular surface of a selected type of human joint socket, the body having one or more holes each extending through the first side and the second side such that if the first side is disposed in contact with an articular surface of the selected type of human joint socket, the longitudinal axis of the hole will extend into bone adjacent the joint socket without passing through the articular surface. In some embodiments, the first side is configured to be disposed in contact with a glenoid such that the central longitudinal axis of each of the one or more holes extends through the scapula adjacent the glenoid. In some embodiments, at least a portion of the first side is convex.

Some embodiments of the present apparatuses further comprise: a pin having a first end, a second end, and a depth indicator, the pin configured to be inserted into the bone adjacent the selected type of human joint socket through one of the one or more holes in the body of the jig to a depth indicated by the depth indicator such that the second end extends a predetermined distance out of the bone. In some embodiments, the depth indicator comprises a mark on the pin corresponding to a portion of the second side of the body of the jig.

Some embodiments of the present apparatuses further comprise: a reamer configured to be disposed over the second end of one of the pin when the first end of the pin is disposed in the bone, and rotated to remove a portion of the bone to form a mating surface on the bone. In some embodiments, the reamer comprises a cutting end, a distal end, and an elongated passage extending from the cutting end toward the distal end, the passage configured to receive at least a portion of one of the one or more pins. In some embodiments, the reamer comprises a shoulder in the passage, the shoulder configured to contact the second end of the pin to limit the depth to which the cutting end can cut. In some embodiments, the shape of the mating surface corresponds to the shape of the coupling side of the body of one of the present devices. In some embodiments, the mating surface and the coupling side are each substantially planar.

Some embodiments of the present kits comprise: one or more of the present devices; and one or more of the present apparatuses. In some embodiments, the device(s) and apparatus(es) are sterile. In some embodiments, the device(s) and apparatus(es) are disposed in a sealed package.

Some embodiments of the present methods (e.g., of repairing a human joint socket) comprise: coupling a device having a pre-formed body to a bone adjacent to a human joint socket, where the body comprises a coupling side and a concave side disposed at a non-parallel angle relative to the coupling side, and the body is coupled to the bone such that the coupling side faces the bone and the concave side augments the articular surface of the joint socket. Some embodiments further comprise: shaping, prior to coupling the body to the bone, the bone to correspond to the shape of the coupling side. In some embodiments, shaping comprises: disposing a jig of one of the present apparatuses such that the first side contacts the articular surface of the joint socket; inserting a pin of one of the present apparatuses into the bone through one of the one or more holes of the body of the jig to a depth indicated by the depth indicator; removing the jig while the pin is disposed in the bone; disposing a reamer of one of the present apparatuses over the second end of the pin and rotating the reamer to shape the bone; and removing the reamer and the pin. In some embodiments, the one or more holes in the body of the jig comprises two holes, and shaping further comprises: inserting a pin of one of the present apparatuses the bone through a second one of the one or more holes in the body of the jig to a depth indicated by the depth indicator; removing the jig while the second pin is disposed in the bone; disposing a reamer of one of the present apparatuses over the second end of the second pin and rotating the reamer to shape the bone; and removing the reamer and the second pin. In some embodiments, coupling comprises inserting one or more screws through the body and into the bone. In some embodiments, the preformed body comprises the pre-formed body of one of the present devices. In some embodiments, the joint socket comprises the glenoid, and where the body is coupled to the bone in which a portion of the glenoid rim is missing.

Any embodiment of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiments depicted in the figures.

DESCRIPTION OF ILLUSTRATIVE EMBODIMENTS

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees, and substantially parallel includes parallel), as understood by a person of ordinary skill in the art. In any embodiment of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Referring now to the drawings, and more particularly to FIGS. 1A-1D, shown therein and designated by the reference numeral 10 is one embodiment of the present devices for repairing and/or augmenting the articular surface of a joint socket (e.g., by restoring the articular curvature and/or the articular rim). In the embodiment shown, device 10 comprises a pre-formed body 14 comprising a coupling side 18 and a concave side 22. In this embodiment, concave side 22 is disposed at a non-parallel angle 26 relative to coupling side 18. For example, in the embodiment shown, angle 26 is between 30 degrees and 60 degrees (e.g., between 40 and 50 degrees). In other embodiments, angle 26 can be less than 30 degrees or more than 60 degrees to enable body 14 to function with various types of joints. In the embodiment shown, body 14 is configured to be coupled to a bone adjacent to a selected type of human joint socket such that the coupling side faces the bone and the concave side augments the articular surface of the joint. For example, in the embodiment shown, body 14 is configured to repair an anterior fracture of a patient's glenoid rim, such as may be caused by anterior shoulder dislocation(s). More particularly, body 14 is configured to be coupled to a human scapula adjacent the glenoid (e.g., an anterior portion of the glenoid) such that the concave side augments an anterior portion of the glenoid rim. Other embodiments can be configured to repair and/or augment the articular surface and/or articular rim of other joints (e.g., can augment the articular surface of the acetabulum in a patient's hip joint).

Figure 4:
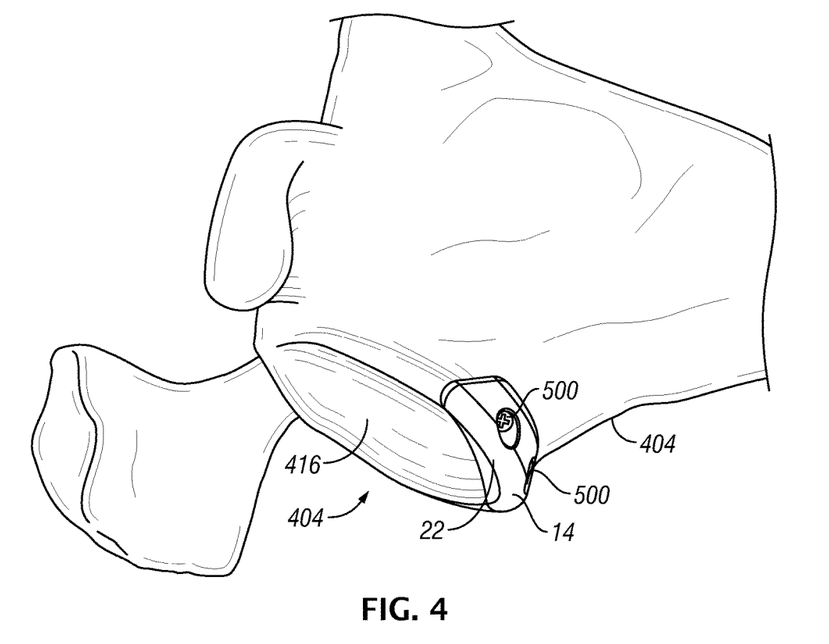
FIG. 4 depicts a perspective view of a human scapula with a device of FIGS. 1A-1D coupled to the anterior glenoid.
Figure 5A:
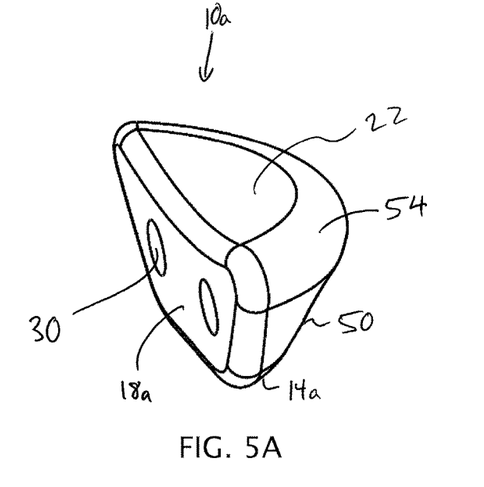
FIGS. 5A-5E depict various views of a second embodiment of the present devices for repairing and/or augmenting the articular surface and/or articular rim of a joint socket.
Figure 5B:
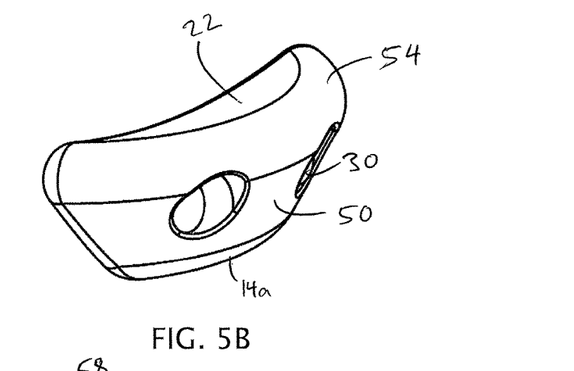
Figure 5C:
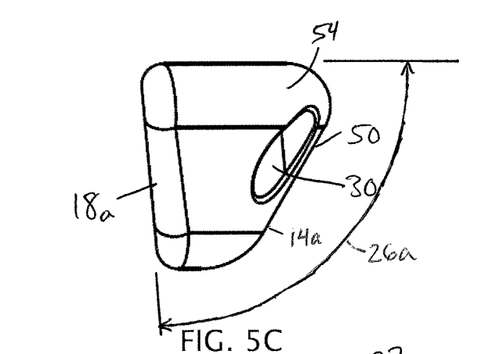
Figure 5D:
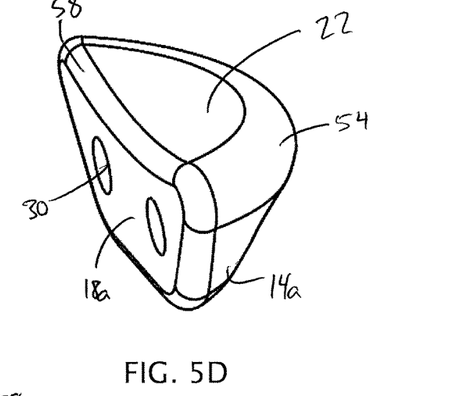
Figure 5E:
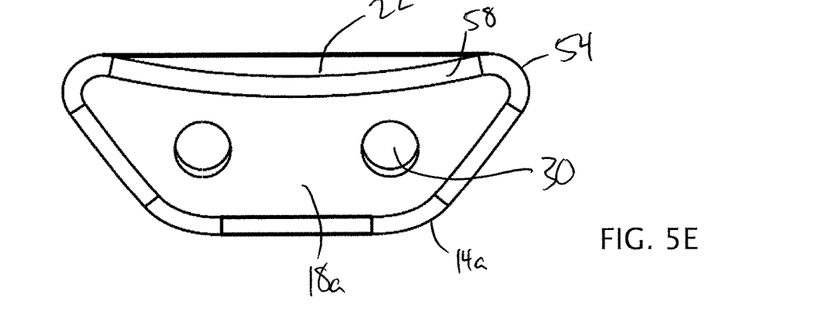
Figure 6A:
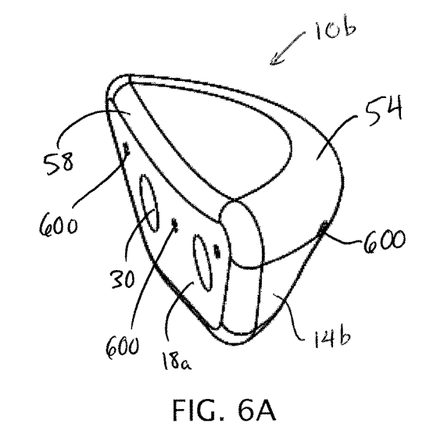
FIGS. 6A-6E depict various views of a third embodiment of the present devices for repairing and/or augmenting the articular surface and/or articular rim of a joint socket.
Figure 6B:
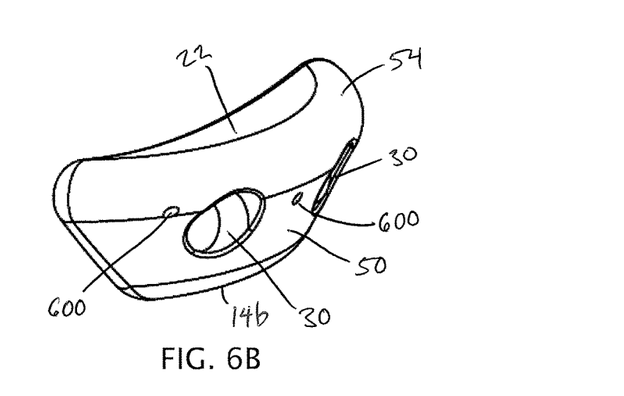
Figure 6C:
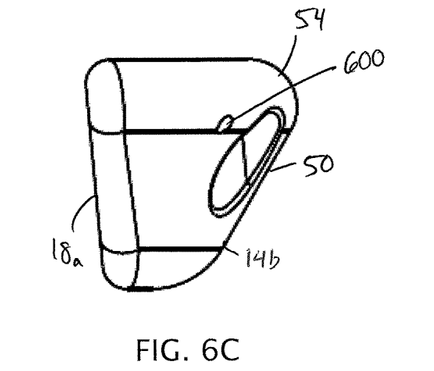
Figure 6D:
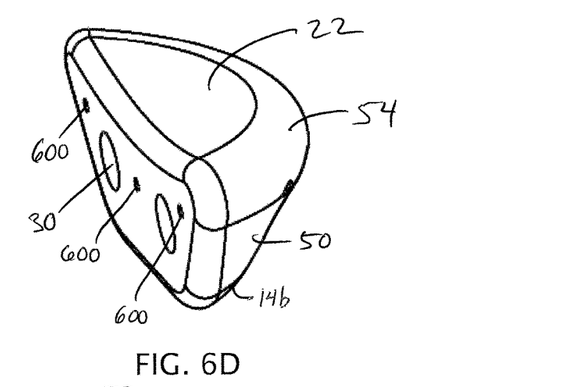
Figure 6E:
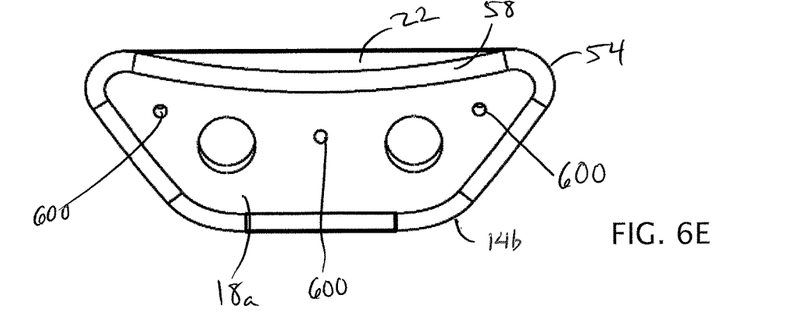

In some embodiments, body 14 is configured to be coupled to the bone by one or more screws (e.g., screws 500 of FIG. 4). For example, in the embodiment shown, body 14 comprises one or more (e.g., two, as shown) holes 30 extending through the body without extending through concave side 22, such that body 14 can be coupled to the bone by one or more screws extending through the one or more holes. In the embodiment shown, each hole 30 has a central longitudinal axis 34 that is not perpendicular to coupling side 18. In other embodiments, axis 34 may be perpendicular to coupling side 18. In the embodiment shown, holes 30 each has an enlarged or countersunk outer portion 34 defining a shoulder 38. In this embodiment, portion 34 is enlarged to receive the head of a screw (e.g., screws 500 of FIG. 4) against shoulder 38 and within the outermost perimeter of body 14.

In some embodiments, body 14 comprises a plurality of projections extending outwardly from coupling side 18 and configured to resist movement of the body relative to the bone. For example, in the embodiment shown, body 14 comprises a plurality of (e.g., conical) spikes 42 configured to extend into the bone adjacent a joint socket when body 14 is coupled to the bone. In other embodiments, projections have any suitable other shape that resists lateral movement of body 14 relative to bone (e.g., in a direction parallel to coupling side 18). In some embodiments, coupling side 18 is configured to permit bone ingrowth into body 14 (e.g., inwardly relative to at least one portion of coupling side 18, such that ingrown bone will resist lateral movement of body 14 relative to the bone. For example, in the embodiment shown, coupling side 18 comprises a plurality of open channels 46 extending parallel to coupling side 18. In other embodiments, coupling side 18 can comprise any suitable features configured to permit bone ingrowth into body 14. For example, in some embodiments, coupling side 18 can be textured (e.g., at least a portion of the coupling side can be at least one of porous and etched). In most embodiments, concave side 22 is substantially smooth (e.g., polished or otherwise devoid of surface irregularities that might otherwise interfere with joint motion when body is coupled to a bone such that concave surface 22 augments the articular surface of the joint).

Body 14 can comprise one or more of a variety of non-biological materials (not harvested from a human patient or other animal). For example, body 14 can comprise one or more of stainless steel, titanium, biocompatible polymer, and/or any other material that permits body 14 to function as described in this disclosure. In some embodiments, body 14 comprises a structural material that defines a plurality of the volume of body 14, and a coating material disposed around the structural material that defines at least a portion of the outermost surface of body 14. For example, the structural material can comprise one or more pores, passages, or interstices (e.g., can be porous) and be substantially-rigid and/or biocompatible (e.g., metal foam, polymer lattice, and/or the like), and/or the coating material can comprise a substantially smooth and hard biocompatible coating (e.g., ceramic, polymer, metallic shell, and/or the like). In such composite embodiments, coupling side can be configured to permit bone ingrowth by configuring the coating material to cover substantially all of concave side 22 but does not cover substantially all of coupling side 18 (e.g., coating material does not cover all or part of coupling side, such that bone ingrowth is permitted into the pores, passages, or interstices of the structural material.

In the embodiment shown, body 14 further includes an outer side 50 that cooperates with concave side 22 to form an outer rim 54 (e.g., a round or radius between outer side 50 and concave side 22). In this embodiment, coupling side 18 and concave side 22 also cooperate to form an inner rim 58 (e.g., a round or radius between coupling side 18 and concave side 22). In the embodiment shown, inner rim 58 is concave, and outer rim 54 is convex. In this embodiment, outer rim 54 is configured to augment the articular rim of the glenoid of a patient.

Figure 1A:
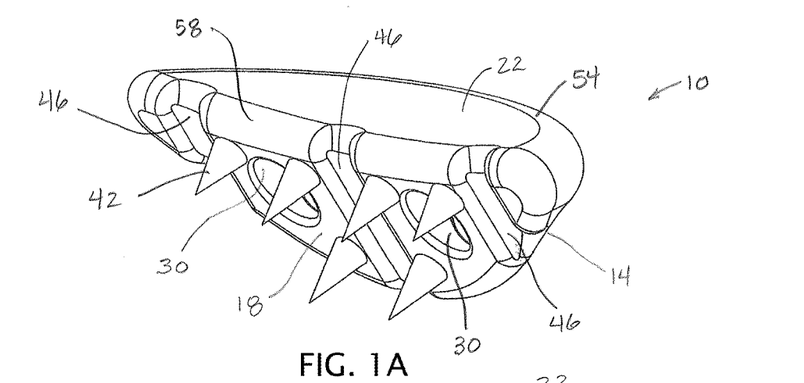
FIGS. 1A-1D depict various views of an embodiment of the present devices for repairing and/or augmenting the articular surface and/or articular rim of a joint socket.
Figure 1B:
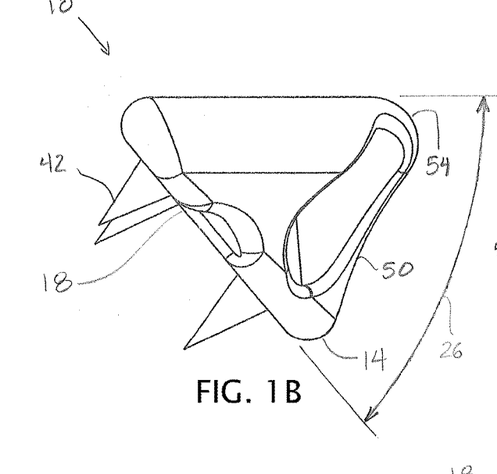
Figure 1C:
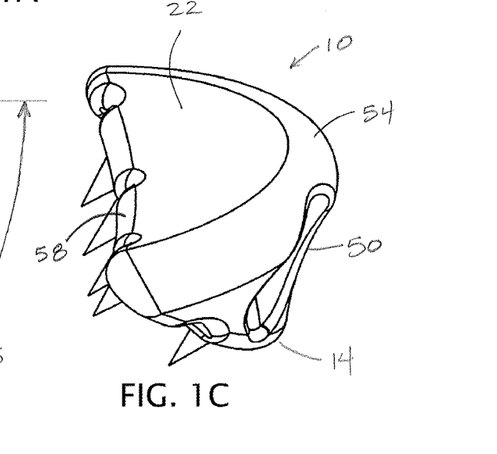
Figure 1D:
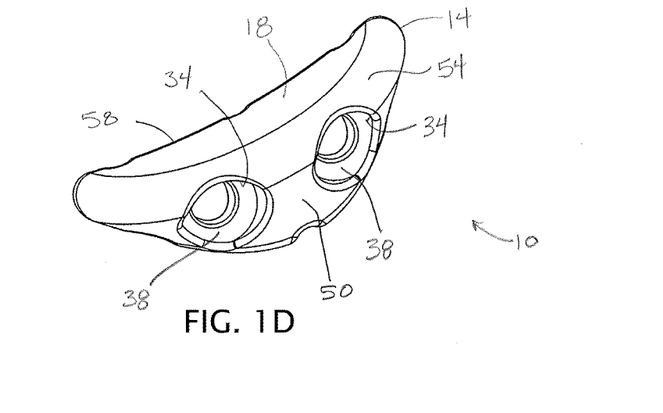
Figure 2:
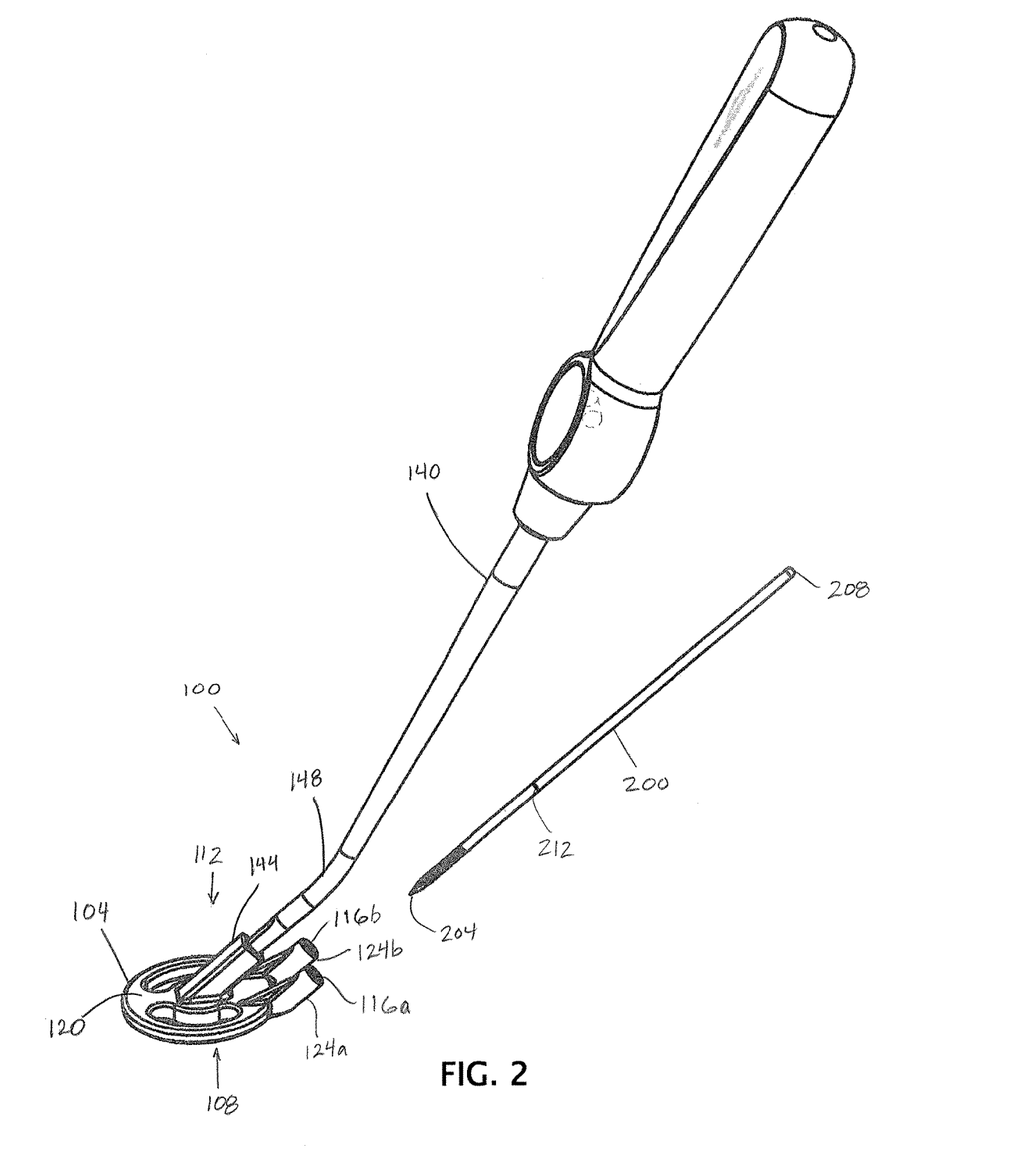
FIG. 2 depicts a perspective view of embodiments of a jig and a pin of the present apparatuses for preparing a bone to be coupled to the device of FIGS. 1A-1D.

Referring now to FIGS. 2-4, shown therein are various components of the present apparatuses for use with device 100, and various steps of exemplary embodiments of the present methods for such use. FIG. 2 depicts a perspective view of embodiments of a jig 100 and a pin 200 of the present apparatuses for preparing a bone to be coupled to device 10. In the embodiment shown, jig 100 has body 104 with a first side 108 configured to be disposed in contact with an articular surface of a selected type human joint socket, and a second side 112. For example, in some embodiments, a portion of first side 108 is convex. For example, in the embodiment shown, the portion of first side 108 corresponding to primary portion 120 is convex and contoured to correspond to the shape of the inferior aspect of the glenoid, such that when in contact with the articular surface of the glenoid, the convex portion indicates the position of jig 100 at which pin(s) 200 should be inserted into the bone, as described in more detail below. In the embodiment shown, body 104 has one or more (e.g., two, as shown) holes 116a, 116b each extending through first side 108 and second side 112 such that if the first side is disposed in contact with an articular surface of the selected type of human joint socket, the longitudinal axis of the hole will extend into bone adjacent the joint socket without passing through the articular surface. For example, in the embodiment shown, body 104 comprises a circular primary portion 120 and one or more (e.g., two, as shown) projections 124a, 124b offset from the center of, primary portion 120 and extending at an angle 128 to distal ends 132a, 132b. In the embodiment shown, angle 128 is between 30 degrees and 60 degrees (e.g., between 40 and 50 degrees). In other embodiments, angle 128 can be less than 30 degrees or more than 60 degrees, to enable jig 100 to function with various types of joints. In the embodiment shown, first side 108 (e.g., primary portion 120) is configured to be disposed in contact with the articular surface of a glenoid such that the central longitudinal axis 136a, 136b of each of the one or more holes 116a, 116b extends through the scapula adjacent the glenoid. In the embodiment shown, jig 100 also comprises: a handle 140 extending from body 104 (e.g., coupled to projection 144 of body 104). In the embodiment shown, handle 140 comprises a bend 144 to discourage rotation of body 104 during use and thereby improve stability and controllability of the jig. In other embodiments, handle 140 may include a forked portion and/or may be U-shaped such that the handle is/can be coupled to the body at two points.

In the embodiment shown, pin 200 has a first end 204, a second end 208, and a depth indicator 212. In this embodiment, pin 200 is configured to be inserted into the bone adjacent the selected type of human joint socket through one of the one or more holes 116a, 116b in body 104 of the jig to a depth indicated by depth indicator 212 such that second end 208 extends a predetermined distance out of the bone. For example, in the embodiment shown, depth indicator 212 comprises a line or other mark printed, engraved, etched, or otherwise visible at a selected point on the pin and corresponding to a portion of second side 108 of body 104 of the jig. In this embodiment, when jig 100 is disposed with first side 108 in contact with the articular surface of a patient's glenoid, pin 200 can be inserted into one of holes 116a, 116b until depth indicator 212 is aligned with the distal end 132a, 132b of the corresponding one of projections 124a, 124b. In the embodiment shown, first end 204 of pin 200 comprises a self-tapping tip 216 and threaded portion 220 such that pin 200 can be inserted to a desired depth relative to a bone and threaded portion 220 will substantially maintain the position of pin 200 relative to the bone.

In some embodiments, the present apparatuses also comprise a reamer 300 (FIG. 3E) configured to be disposed over second end 208 of the pin when first end 204 of the pin is disposed in the bone, and the reamer rotated to remove a portion of the bone to form a mating surface on the bone. For example, in the embodiment shown, reamer 300 comprises a proximal cutting end 304, a distal end 308, and shaft 312 with an elongated passage 316 extending from cutting end 304 toward distal end 308 and configured to receive second end 208 of pin 200. In this embodiment, cutting end 304 has a larger diameter relative to shaft 312 and is configured such that if the reamer is rotated around shaft 312, cutting end 304 will cut away bone to contour a mating surface on the bone. In the embodiment shown, shaft 312 comprises a shoulder or other stop (e.g., proximal end) 320 in passage 316 configured to contact second end 208 of pin 200 to limit the depth to which cutting end 304 of the reamer can cut. For example, when pin 208 is inserted into bone to a desired depth (e.g., indicated by depth indicator 212 of pin 200 and distal end 132a of projection 124a of jig 100), shoulder 316 is configured to ensure that the mating surface of the bone is formed at a desired depth or position. In this embodiment, cutting end 304 of the reamer is configured to form a mating surface on the bone that corresponds to the shape of coupling side of body 14 of device 10 (e.g., substantially planar).

Figure 3A:
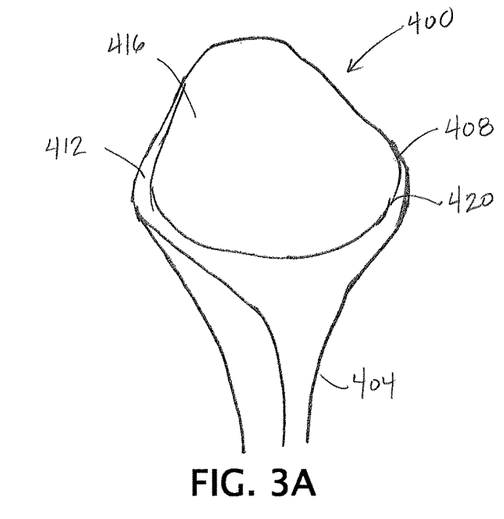
FIG. 3A depicts a perspective view of a normal human glenoid.
Figure 3B:
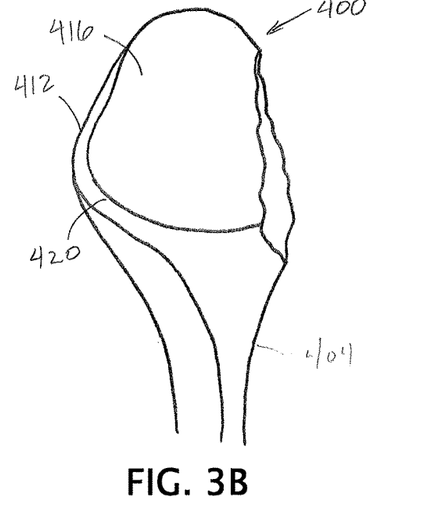
FIGS. 3B-3G depict various views of stages of the present methods of repairing an anterior glenoid rim fracture with the device of FIGS. 1A-1D, using the apparatus of FIG. 2.

Certain embodiments of the present methods will now be described with reference to FIGS. 3A-3G and 4. FIG. 3A depicts a normal glenoid portion 400 of a human scapula 404. Glenoid 400 includes an anterior side 408, a posterior side 412, an articular surface 416, and a rim 420. FIG. 3B depicts a similar human glenoid portion 400 of a human scapula 404, but with an anterior portion of rim 420 (and articular surface 416) broken away from the glenoid.

Some embodiments of the present methods repairing a human joint socket (e.g., glenoid), comprise: coupling a device (e.g., 10) with a pre-formed body (e.g., 14) to a bone adjacent to a human joint socket, where the body comprises a coupling side (e.g. 18) and a concave side (e.g., 22) disposed at a non-parallel angle relative to the coupling side, and the body is coupled to the bone such that the coupling side faces the bone and the concave side augments the articular surface of the joint socket.

Figure 3C:
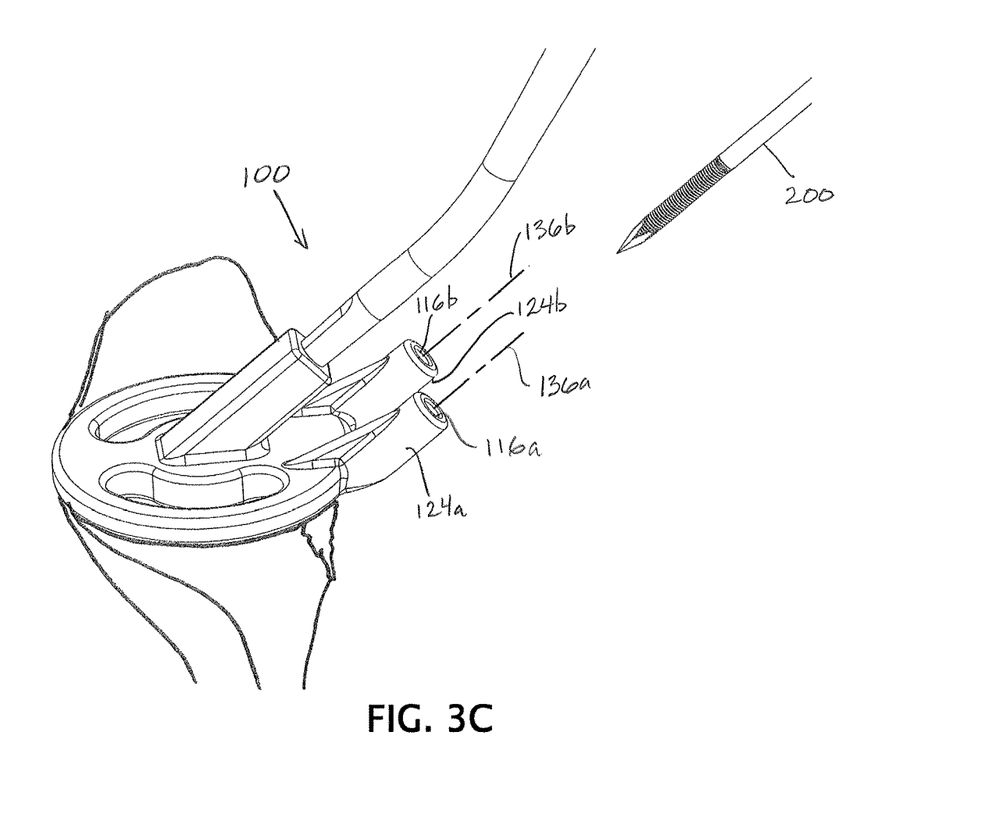
Figure 3D:
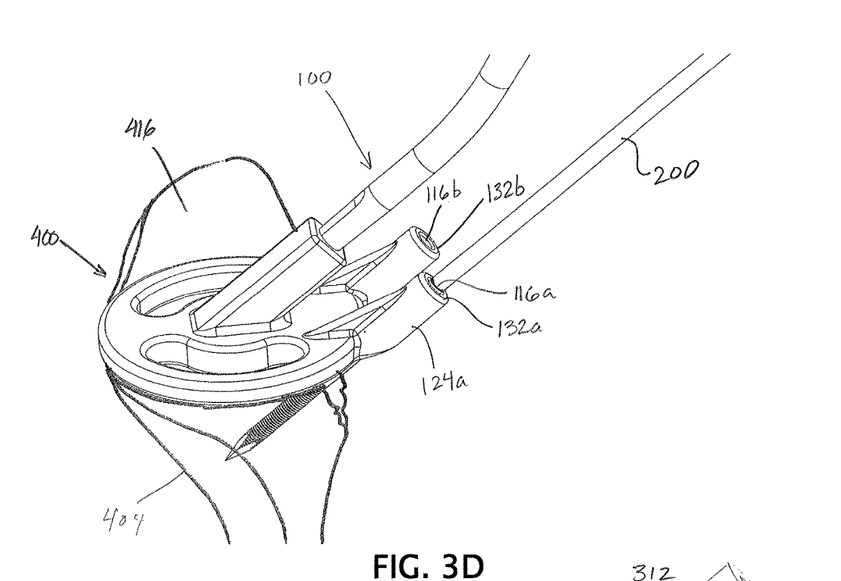
Figure 3E:
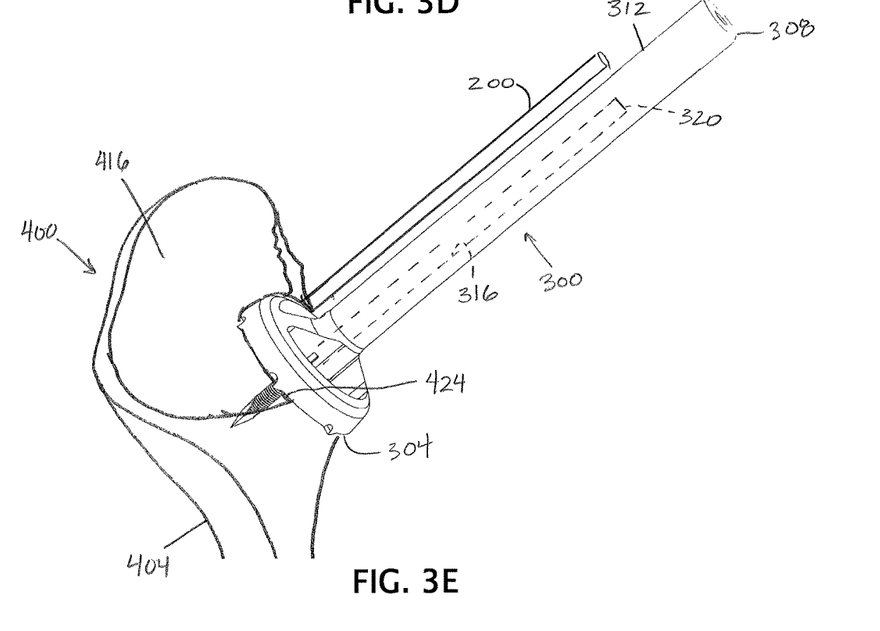

Some embodiments of the present methods further comprise: shaping, prior to coupling the body to the bone, the bone to correspond to the shape of the coupling side. For example, in some embodiments, shaping comprises: disposing a jig (e.g., 100) such that first side 108 contacts articular surface (e.g., 416) of the joint socket, as shown in FIG. 3C. Some embodiments further comprise inserting a pin 200 into the bone (e.g., clavicle 404) through one (116a) of the one or more holes of the body of the jig to a depth indicated by depth indicator 212, as shown in FIG. 3D. In some embodiments, jig 200 is then removed (from pin 200) while pin 200 is disposed in the bone, such as, for example, by pulling the jig away from the bone over pin 200. Some embodiments further comprise disposing reamer 300 over second end 208 of the pin and rotating the reamer to shape the bone (e.g., to shape a mating surface 424), as shown in FIG. 3E. Once the mating surface of the bone is shaped, reamer 300 is removed from the pin 200, and pin 200 can be removed from the bone.

In embodiments using jig 100 or other jigs having two or more holes (e.g., 116a, 116b), the present methods can further comprise inserting a second pin 200 or inserting the same pin 200 a second time. For example, in some embodiments, two pins 200 are inserted through holes 116a, 116b before removal of jig 100 from the bone, and reamer 300 is disposed and rotated sequentially over each pin 200 while both pins are disposed in the bone, as shown in FIG. 3E. In other embodiments, before the first pin or pin placement is removed, the jig is re-placed over the first pin such that the first side contacts the articular surface of the joint socket, and a pin 200 is then inserted into the bone through a second one (116b) of the one or more holes in the body of the jig to a depth indicated by the depth indicator (212). In some embodiments, a single pin is left in place until the jig is re-placed and then removed while the jig is in place and inserted into second hole 116b. In other embodiments, a second pin 200 is inserted into second hole 116b while the first pin is still disposed in the bone and through first hole 116a, and then the first pin is removed while the second pin remains disposed in the bone. Once the second pin is disposed in the bone at the selected depth, the jig can then be removed from the second pin while the second pin is disposed in the bone, and reamer 300 disposed over second end 208 of the second pin and rotated to shape the bone (to further form the mating surface of the bone. Because the first and second pins are inserted into the bone at substantially parallel angles and to substantially equal depths, the mating surface formed by the first and second applications of the reamer(s) are substantially aligned and form a substantially continuous mating surface on the bone. After the second application of the reamer (on the second pin), the reamer and second pin can be removed from the bone.

Figure 3F:
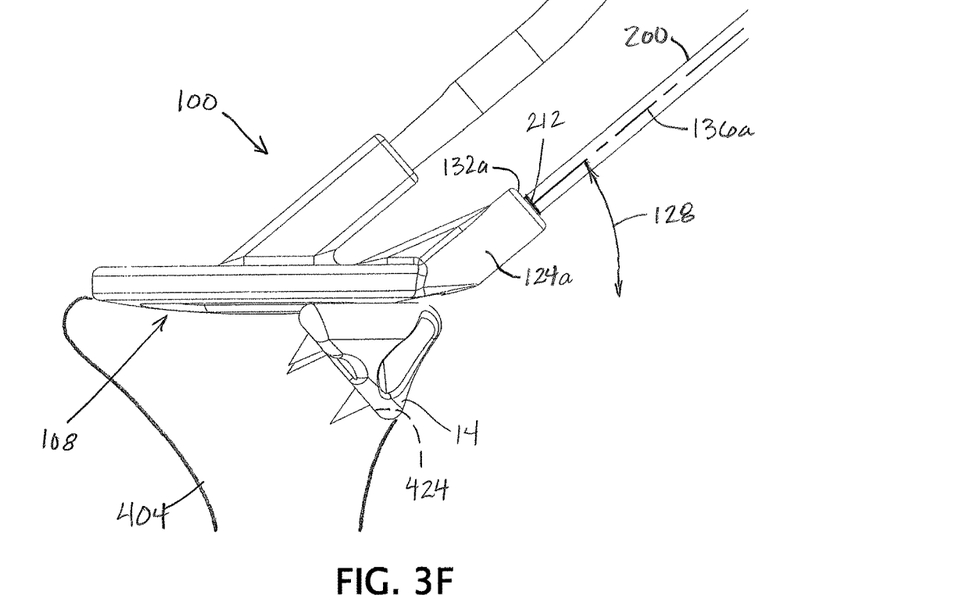
Figure 3G:
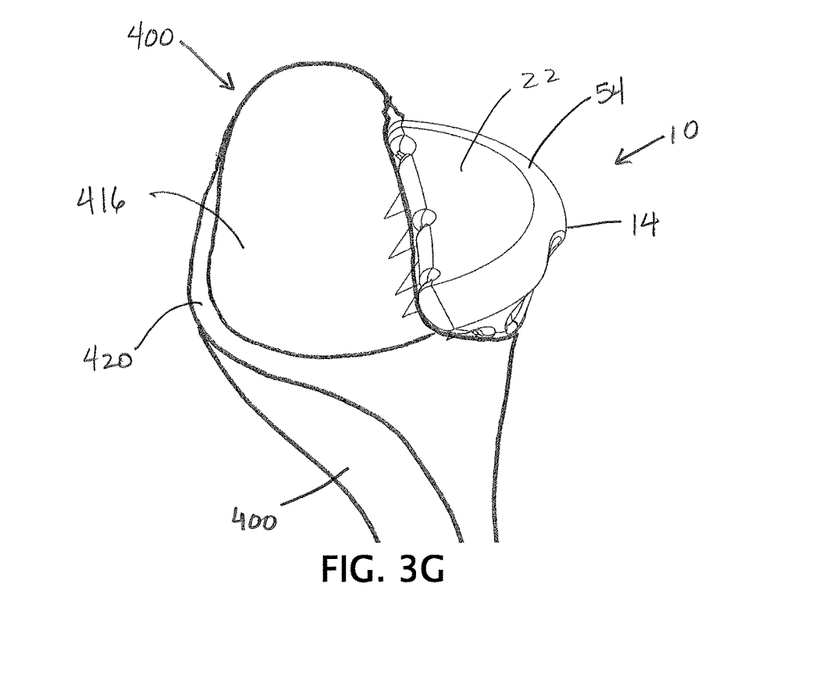

Once the bone has been shaped, device 10 can be disposed adjacent to the bone with coupling side 18 facing mating surface 424, as shown in FIG. 3F (e.g., without pin 200 in place). For example, jig 100 can be disposed with first side 108 in contact with the articular surface of the joint to ensure appropriate placement and alignment of body 14 of the device. With body 14 in alignment, screws 500 (e.g., self-tapping, biocompatible screws) can be inserted into the bone through holes 30 to secure body 14 to the bone (e.g., to the scapula, as illustrated in FIG. 4). As shown in FIG. 3G, when coupled to scapula 404, concave surface 22 is configured to augment the articular surface (e.g., substantially match or correspond to the articular curvature) to increase the effective articular surface area for the joint, and/or to augment the articular rim 420 to provide a physical barrier to dislocation of the shoulder joint.

FIGS. 5A-5E depict various views of a second embodiment 10a of the present devices for repairing and/or augmenting the articular surface and/or articular rim of a joint socket. Device 10a is similar in many respects to device 10 and, as such, the differences in device 10a will primarily be described here. In the embodiment shown, device 10a comprises a pre-formed body 14a having a coupling side 18a and a concave side 22. In this embodiment, concave side 22 disposed at a non-parallel angle 26a relative to coupling side 18a. In the embodiment shown, angle 26a is greater than 60 degrees (e.g., between 60 and 90 degrees, between 80 and 90 degrees, and/or substantially equal to 85 degrees). As with device 10, device 10a is configured to be coupled to a bone adjacent to a selected type of human joint socket such that the coupling side faces the bone and the concave side augments the articular surface of the joint. In the embodiment shown, body 14a comprises a biological material such as, for example, a cortical bone allograft that is shaped from donor bone tissue.

FIGS. 6A-6E depict various views of a third embodiment 10b of the present devices for repairing and/or augmenting the articular surface and/or articular rim of a joint socket. Device 10b is similar in many respects to device 10a and, as such, the differences in device 10b will primarily be described here. As shown, device 10b further comprises two or more suture holes 600 each extending through body 14a without extending through concave side 22. Suture holes 600 are configured to enable suturing soft tissue adjacent to the joint to body 14a. For example, suture holes 600 permit reattachment of capsular soft tissues, such as, for example, to reinforce a compromised rotator cuff.

Figures 7A, 7B:
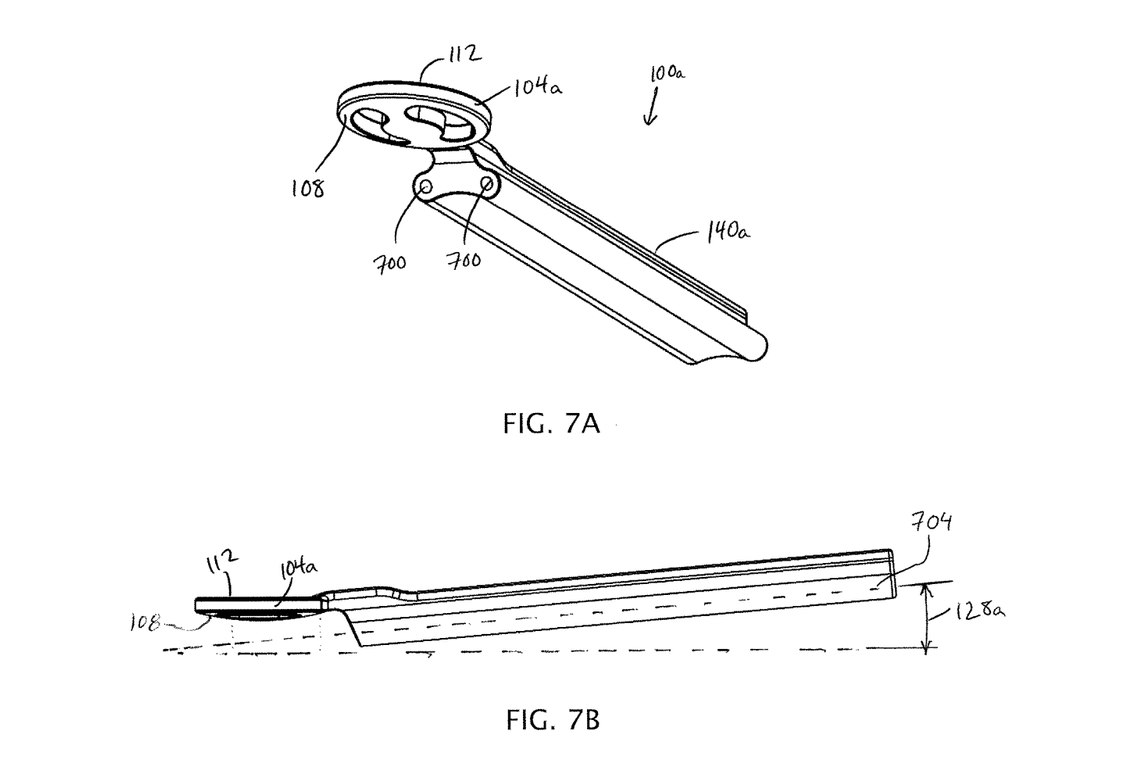
FIG. 7A-7C depict various views of a second embodiment of a jig of the present apparatuses for preparing a bone to be coupled to the device of FIGS. 5A-5E.
Figure 7C:
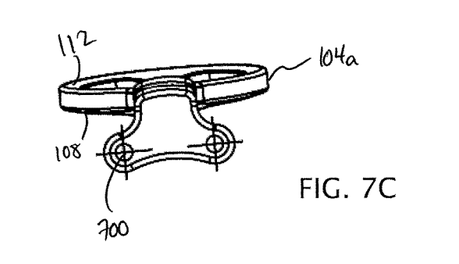
Figure 8A:
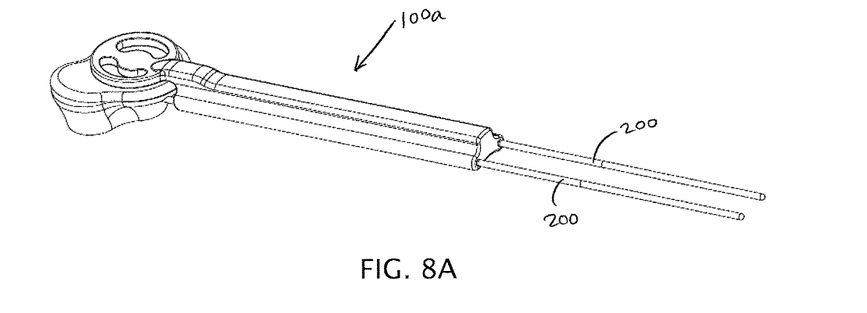
FIGS. 8A-8D depict various views of stages of the present methods of repairing an anterior glenoid rim fracture with the device of FIGS. 5A-5E, using the apparatus of FIG. 6.
Figure 8B:
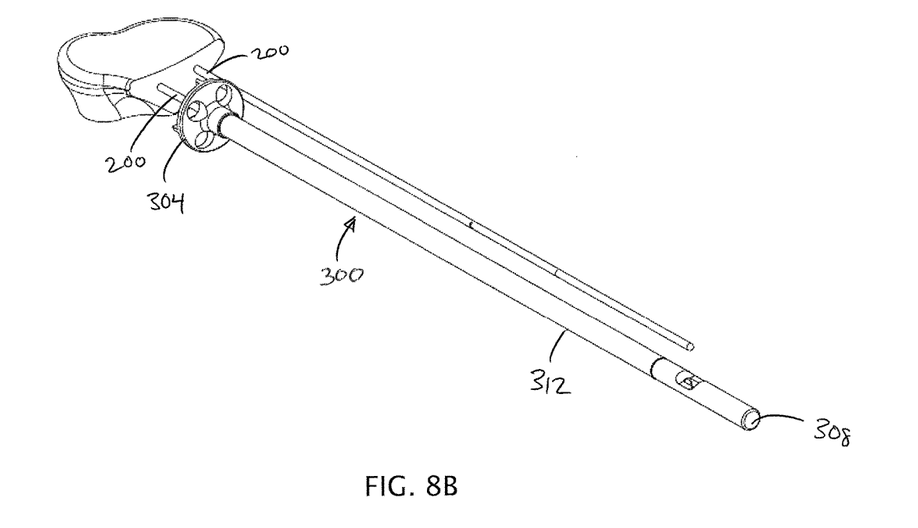
Figure 8C:
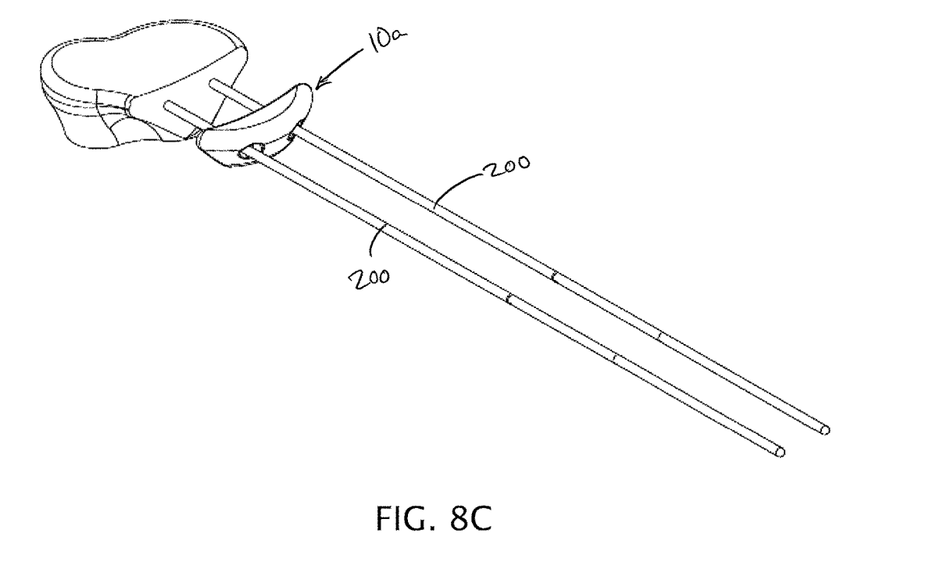
Figure 8D:
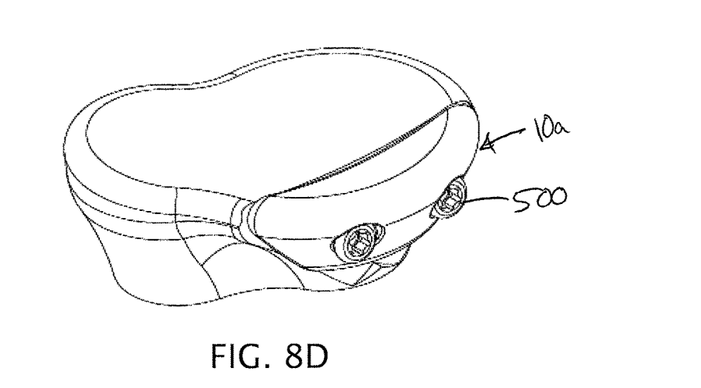

FIG. 7A-7C depict various views of a second embodiment 100a of the present jigs, with jig 100a being configured for preparing a bone to be coupled to the device of FIGS. 5A-5E. Jig 100a is similar in many respects to jig 100 and, as such, the differences in jig 100a will primarily be described here. In the embodiment shown, jig 100a has a body 104a with a first side 108 configured to be disposed in contact with an articular surface of a selected type human joint socket, and a second side 112. In this embodiment, however, body 104a differs from body 104 of jig 100 in that body 104a does not define guide holes (e.g., 116a, 116b) for pins. Instead, in the embodiment shown, jig 100a includes a handle 140a extending from body 104a and defining one or more elongated channels 700 each extending longitudinally through the handle. In this embodiment, channels 700 are offset from first side 108 of the body such that if the first side (108) is disposed in contact with an articular surface of a joint socket, a central longitudinal axis 704 will extend into bone adjacent the joint socket without passing through the articular surface. In some embodiments, first side 108 is configured to be disposed in contact with a glenoid such that the central longitudinal axis (e.g., 704) of each of the one or more elongated channels (e.g., 700) extends through the scapula adjacent the glenoid. In the present embodiment, the length of at least one elongated channel 700 is at least 5 centimeters (e.g., greater than 10 cm, and/or 20 cm (e.g., 22.86 cm or 9 inches), but may be shorter in other embodiments. In this embodiment, angle 128a between first side 108 of body 104a and central longitudinal axis 704 of channels 700 is less than 30 degrees (e.g., between 0 and 20 degrees, between 0 and 10 degrees, and/or substantially equal to 5 degrees).

The use of devices 10a, 10b and jig 100a proceeds in similar fashion to that described above for FIGS. 3B-3G. For example, FIGS. 8A-8D depict various views of stages of the present methods of repairing an anterior glenoid rim fracture with device 10a and jig 100a.

Some embodiments of the present kits comprise: one or more devices 10, 10a, and/or 10b and one or more of the present apparatuses (e.g., each including a jig 100 or 100a, at least one pin 200, and at least one reamer 300). For example, some embodiments of the present kits comprise a device (10, 10a, and/or 10b), a jig (100 and/or 100a), two or more pins 200, and a reamer 300. In some embodiments, the device(s) and apparatus(es) are sterile and/or disposed in a sealed package (e.g., a polymer tray with a sealing file).

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices, apparatuses, kits, and methods are not intended to be limited to the particular forms disclosed. Rather, they include all modifications and alternatives falling within the scope of the claims, and embodiments other than the one shown may include some or all of the features of the depicted embodiment. For example, jig 100 and reamer 300 can be configured such only one hole is included in the body of the jig to receive and position a pin 200 (e.g., in the embodiment shown, the diameter of reamer 300 is such that two pins and two applications of reamer to the bone in two different positions will generally be required for form the mating surface on the bone; but, in other embodiments, jig 100 can comprise a single, central hole for positioning the pin, and the cutting end of the reamer can have a diameter that is large enough to form the mating surface with a single application of the reamer. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An implant comprising:
   a pre-formed body comprising:
      a coupling side, an outer side, and a concave side disposed at an angle of between 60 and 90 degrees relative to the coupling side, the outer side extending between the coupling side and the concave side, the coupling side having a planar portion that extends a majority of a distance between the concave side and the outer side, the coupling side cooperating with the outer side to form a first convex surface extending between the coupling side and the outer side to define a first convex rim, and the coupling side cooperating with the concave side to form a second convex surface extending between the coupling side and the concave side to define a concave rim; and
      multiple through holes each of which extends continuously through the outer side, the body, and the coupling side, without also extending through the concave side, the multiple through holes comprising:
         one or more screw holes each having a first diameter; and
         one or more suture holes each having a second diameter that is smaller than the first diameter;
   wherein the body is configured to be coupled to a bone adjacent to a selected type of human joint socket such that the coupling side contacts the bone and the concave side augments an articular surface of the joint; and
   wherein the body comprises a biological material, the biological material comprises bone material.

2. The implant of claim 1, where the body is configured to be coupled to a scapula adjacent a glenoid such that the concave side augments an anterior portion of a rim of the glenoid, and where the concave side is disposed at the angle relative to the planar portion of the coupling side.

3. The implant of claim 1, where the one or more screw holes include multiple screw holes, and where the body is configured to be coupled to the bone by one or more screws extending through the one or more screw holes.

4. The implant of claim 1, where the biological material comprises cortical bone.

5. The implant of claim 1, where the outer side cooperates with the concave side to form a third convex surface extending between the outer side and the concave side to define a second convex rim.

6. The implant of claim 3, where the one or more suture holes include multiple suture holes, and where the concave side is free of through holes.

7. The implant of claim 1, where each of the one or more suture holes are adapted to suture soft tissue adjacent to the joint, the one or more screw holes include a first screw hole and a second screw hole, a first suture hole of the one or more suture holes is positioned between the first screw hole and the second screw hole, and each of the first suture hole, the first screw hole, and the second screw hole extend through the biological material.

8. The implant of claim 3, where the one or more screw holes each has a central longitudinal axis that is perpendicular to the coupling side, and each of the one or more screw holes includes a countersunk portion proximate to the outer side.

9. The implant of claim 4, where the concave side is substantially smooth, and where each of the multiple through holes extends through the planar portion of the coupling side.

10. The implant of claim 5, further comprising one or more protrusions extending from the coupling side.

11. An implant comprising:
a pre-formed body comprising:
a coupling side, an outer side, and a concave side disposed at a non-parallel angle relative to the coupling side, the outer side extending between the coupling side and the concave side, the coupling side having a planar portion that extends a majority of a distance between the concave side and the outer side, the outer side cooperating with the concave side to form a first convex surface extending between the outer side and the concave side to define a first convex rim, the coupling side and the outer side cooperating to form a second convex surface extending between the coupling side and the outer side to define a second convex rim, and the coupling side and the concave side cooperate to form a third convex surface extending between the coupling side and the concave side to define a concave rim; and
multiple through holes each of which extends continuously through the outer side, the body, and the coupling side, without also extending through the concave side, the multiple through holes comprising:
one or more screw holes each having a first diameter; and
one or more suture holes each having a second diameter that is smaller than the first diameter;
wherein the body is configured to be coupled to a bone adjacent to a selected type of human joint socket such that the coupling side contacts the bone and the concave side augments an articular surface of the joint; and
wherein the body comprises bone material.

12. The implant of claim 11, where the one or more screw holes enable the body to be coupled to the bone by one or more screws extending through the one or more screw holes.

13. The implant of claim 12, where each of the one or more suture holes are adapted to suture soft tissue adjacent to the joint.

14. The implant of claim 11, where the body further comprises a biological material.

15. The implant of claim 11, where the bone material comprises cortical bone.

16. An apparatus comprising:
a pre-formed body of an implant configured to be coupled to bone adjacent to a joint socket,
the pre-form body comprising:
a coupling side having a planar portion configured to be coupled to the bone,
a concave side disposed at an angle relative to the coupling side and configured to augment an articular surface of the joint socket, the coupling side and the concave side cooperate to form a first convex surface extending between the coupling side and the concave side to define a concave rim,
an outer side extending between the coupling side and the concave side, the coupling side and the outer side cooperating to form a second convex surface extending between the coupling side and the outer side to define a convex rim,
first and second screw holes extending continuously through the outer side and the coupling side, without also extending through the concave side, and
a first suture hole extending continuously through the outer side and the coupling side, without also extending through the concave side,
wherein a diameter of the first suture hole is smaller than a diameter of each of the first and second screw holes, and
wherein the pre-formed body comprises bone material.

17. The apparatus of claim 16, where the first suture hole is positioned between the first screw hole and the second screw hole.

18. The apparatus of claim 17, where the bone material comprises cortical bone, and where the coupling side has a single planar portion configured to be coupled to a planar surface of the bone.

19. The apparatus of claim 17, where the pre-form body further comprises:
a second suture hole extending continuously through the outer side and the coupling side, and
a third suture hole extending continuously through the outer side and the coupling side,
where the first screw hole is positioned between the first suture hole and the second suture hole, and
where the second screw hole is positioned between the first suture hole and the third suture hole.

* * * * *